(12) United States Patent
Kirchnavy

(10) Patent No.: US 10,739,255 B1
(45) Date of Patent: Aug. 11, 2020

(54) TRACE MOISTURE ANALYZER INSTRUMENT, GAS SAMPLING AND ANALYZING SYSTEM, AND METHOD OF DETECTING TRACE MOISTURE LEVELS IN A GAS

(71) Applicant: Advanced Micro Instruments, Inc., Huntington Beach, CA (US)

(72) Inventor: Steven Kirchnavy, Orange County, CA (US)

(73) Assignee: ADVANCED MICRO INSTRUMENTS, INC., Huntington Beach, CA (US)

( * ) Notice: Subject to any disclaimer, the term of this patent is extended or adjusted under 35 U.S.C. 154(b) by 131 days.

(21) Appl. No.: 15/835,903

(22) Filed: Dec. 8, 2017

Related U.S. Application Data

(60) Provisional application No. 62/480,322, filed on Mar. 31, 2017.

(51) Int. Cl.
| | | |
|---|---|---|
| *G01N 21/3554* | (2014.01) | |
| *G01N 21/3504* | (2014.01) | |
| *G01N 21/01* | (2006.01) | |
| *G01N 21/359* | (2014.01) | |
| *G01N 21/39* | (2006.01) | |

(52) U.S. Cl.
CPC ..... *G01N 21/3554* (2013.01); *G01N 21/3504* (2013.01); *G01N 21/359* (2013.01); *G01N 21/39* (2013.01); *G01N 2021/0175* (2013.01); *G01N 2021/354* (2013.01); *G01N 2021/399* (2013.01)

(58) Field of Classification Search
CPC .......... G01N 21/3554; G01N 21/3504; G01N 21/359; G01N 21/39; G01N 2021/0175; G01N 2021/354; G01N 2021/399
See application file for complete search history.

(56) References Cited

U.S. PATENT DOCUMENTS

| | | | | |
|---|---|---|---|---|
| 4,840,706 | A | * | 6/1989 | Campbell .......... G01N 21/3554 162/198 |
| 6,657,198 | B1 | | 12/2003 | May |
| 7,132,661 | B2 | | 11/2006 | May |
| 7,196,786 | B2 | * | 3/2007 | DiFoggio ................. G01V 8/02 356/301 |
| 7,339,168 | B2 | | 5/2008 | May |
| 8,547,554 | B2 | | 10/2013 | Liu et al. |
| 2004/0079887 | A1 | * | 4/2004 | May ................... G01N 21/3504 250/343 |
| 2008/0088821 | A1 | * | 4/2008 | Hurvitz .............. G01N 21/0332 356/51 |

(Continued)

OTHER PUBLICATIONS

Wagner, "Using OMEGA data to determine the optical depth of water vapor absorption bands in the Martian atmosphere", Nov. 17, 2006, University of Texas at San Antonio, 1st Annual MORE Science Colloquium, pp. 83-93. (Year: 2006).*

(Continued)

*Primary Examiner* — David P Porta
*Assistant Examiner* — Jeremy S Valentiner
(74) *Attorney, Agent, or Firm* — John J. Connors; Connors & Assoc.

(57) ABSTRACT

An analyzer instrument, gas sampling and analyzing system, and method are disclosed for detecting water vapor in gas using tunable diode laser absorption spectroscopy at a wavelength of 1871 nm plus or minus 2 nm.

3 Claims, 7 Drawing Sheets

(56) References Cited

U.S. PATENT DOCUMENTS

| | | | | |
|---|---|---|---|---|
| 2008/0092648 | A1* | 4/2008 | Zhou | G01N 21/3504 |
| | | | | 73/335.01 |
| 2009/0078870 | A1* | 3/2009 | Haruna | B60R 1/00 |
| | | | | 250/330 |
| 2014/0104615 | A1* | 4/2014 | Kaneko | G01N 21/3554 |
| | | | | 356/432 |
| 2016/0084757 | A1* | 3/2016 | Miron | G01N 21/39 |
| | | | | 356/437 |
| 2018/0266944 | A1* | 9/2018 | Waxman | G01J 3/42 |

OTHER PUBLICATIONS

University of Texas at San Antonio, MORE Science Colloquium, www.utsa.edu/LRSG/MOREScience/colloquium.html—website captured on Sep. 5, 2019 documenting the 1st Colloquium being held on Nov. 17, 2006. (Year: 2006).*
U.S. Appl. No. 62/480,499, filed Apr. 2, 2017, Steven Kirchnavy.
U.S. Appl. No. 15/782,697, filed Oct. 12, 2017, Steven Kirchnavy.

* cited by examiner

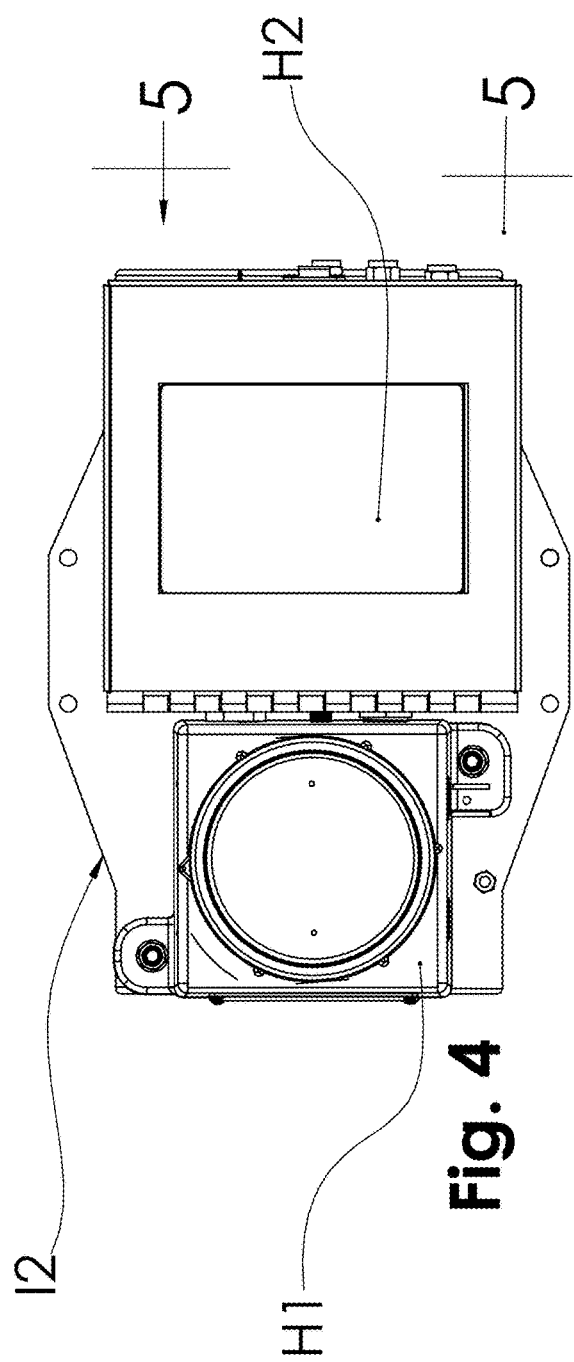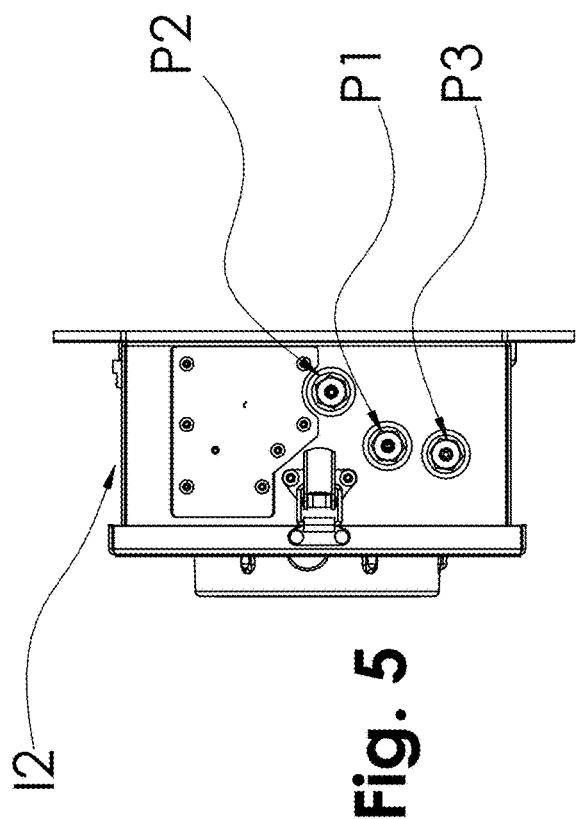

TRACE MOISTURE ANALYZER INSTRUMENT, GAS SAMPLING AND ANALYZING SYSTEM, AND METHOD OF DETECTING TRACE MOISTURE LEVELS IN A GAS

INCORPORATION BY REFERENCE

This utility application claims the benefit under 35 USC § 119(e) of U.S. Provisional Patent Applications No. 62/480,322, entitled "Trace Moisture Analyzer Instrument And Method Of Detecting Trace Moisture Levels In A Gas," filed Mar. 31, 2017, and No. 62/480,499, entitled "Gas-Sampling Device and Method," filed Apr. 2, 2017; and also claims the benefit under 35 USC § 120 of U.S. Utility patent application Ser. No. 15/782,697, entitled "Gas Sampling Device and Method," filed Oct. 12, 2017. These related applications are incorporated herein by reference and made a part of this application. If any conflict arises between the disclosure of the invention in this utility application and that in the related provisional applications, the disclosure in this utility application shall govern. Moreover, any and all U.S. patents, U.S. patent applications, and other documents, hard copy or electronic, cited or referred to in this application are incorporated herein by reference and made a part of this application.

DEFINITIONS

The words "comprising," "having," "containing," "holding," and "including," and other grammatical forms thereof, are intended to be equivalent in meaning and be open ended in that an item or items following any one of these words is not meant to be an exhaustive listing of such item or items, nor meant to be limited to only the listed item or items.

The words "trace amounts of water vapor in a gas" means less than 1000 parts of water vapor per million by volume (ppmv) of the gas in which the water vapor is dispersed.

The word "rectangular" includes square.

The word "block" means a rigid structure that is capable of being acted upon to form therein a gas passageway, or a plurality of rigid structures that may be assembled into a compact, rigid assembly having therein a gas passageway.

The words "block member" means either a single, unitary block or a plurality of assembled blocks forming a compact, rigid assembly.

BACKGROUND

Laser spectroscope instruments for measuring trace amounts of moisture in natural gas are discussed in U.S. Pat. Nos. 6,657,198; 7,132,661; 7,339,168; and, 8,547,554. Companies making such instruments include SpectraSensors, Inc. (SSI), the first company to develop a commercial sensor for this application, Ametek, General Electric (GE), and the assignee of this patent application, Advanced Micro Instruments, Inc. (AMI). Tunable diode laser absorption spectroscopy (TDLAS) is the technique used by these instruments for measuring the concentration of certain species such as methane (CH4), water vapor, and many more, in a gaseous mixture. The advantage of TDLAS over other techniques for trace concentration measurement is its ability to achieve very low detection limits and to eliminate interference from absorption by gases other than the gas species of interest.

Apart from concentration, it is also possible to determine the temperature, pressure, velocity and mass flux of the gas under observation. TDLAS is by far the most common laser based absorption technique for quantitative assessments of species in gas phase. A basic TDLAS setup consists of tunable diode laser light source, transmitting (i.e. beam shaping) optics, optically accessible absorbing medium, receiving optics and detector/s. The emission wavelength of the tunable diode laser, viz. vertical-cavity surface-emitting laser, DFB diode laser, etc., is tuned over the characteristic absorption lines of a species in the gas in the path of the laser beam. This causes a reduction of the measured signal intensity, which can be detected by a photodiode, and then used to determine the gas concentration and other properties as described later.

Different diode lasers types are used based on the application and the wavelength of absorption by the gas species of interest. Typical laser types are InGaAsP/InP (in the wavelength range of 900 nm to 1.6 µm), InGaAsP/InAsP (in the wavelength range of 1.6 µm to 2.2 µm), etc. These lasers can be tuned over a narrow wavelength range by either adjusting their temperature or by changing injection current density into the gain medium. While temperature changes allow tuning over 100 cm$^{-1}$, it is limited by slow tuning rates (a few hertz), due to the thermal inertia of the system. On the other hand, adjusting the injection current can provide tuning at rates as high as ~10 GHz, but it is restricted to a smaller range (about to 2 cm$^{-1}$) over which the tuning can be performed. The typical laser line width is of the order of 10-3 cm$^{-1}$ or smaller. Additional tuning and line width narrowing methods include the use of extra cavity dispersive optics. The basic principle behind the TDLAS technique is simple. The focus here is on a single absorption line in the absorption spectrum of a particular species of interest. To start with, the wavelength of a diode laser is tuned over a particular absorption line of interest and the intensity of the transmitted radiation is measured. The transmitted intensity can be related to the concentration of the species present by the Beer-Lambert law.

Water ($H_2O$) can be measured in natural gas using high-resolution laser absorption spectroscopy where a single vibration-rotation feature of $H_2O$ is targeted at a very specific wavelength. As with all molecules that absorb light in the infrared wavelength region, the absorption spectrum consists of many (hundreds to thousands) of individual absorption "lines" within a broad (in terms of wavelength range) "band." These absorption bands occur throughout the electromagnetic spectrum from the ultraviolet (UV) to the far infrared. For the measurement of $H_2O$ in natural gas (consisting mostly of methane $CH_4$), the best wavelength region to use is near 1.9 microns, or 1900 nm. The primary reasons are that lasers are available in this region that are economically viable for an industrial gas sensor, and there is somewhat of a gap in the strong $CH_4$ absorption that is present throughout most of the infrared wavelength region. For water vapor in natural gas, SpectraSensors, Inc. was the first company to develop a commercial sensor for this application starting around the year 2000. Since that time both Ametek and GE have similar systems on the market. All use lasers operating just short of 1900 nm.

SUMMARY

I have discovered that the wavelength of 1871 nanometers (nm) plus or minus 2 nm is the ideal wavelength to conduct tunable diode laser absorption spectroscopy (TDLAS) for detecting trace amounts of water vapor in a gas. Capitalizing on this discovery, my analyzer instrument, gas sampling and analyzing system, and method are used to detect trace amounts of moisture in natural gas, consisting mainly of methane, and other gases that do not have interfering absorption lines such as, for example, air, nitrogen, argon, hydrogen, helium, and carbon dioxide ($CO_2$).

The claims that follow define my analyzer instrument, gas sampling and analyzing system, and method, distinguishing them from the prior art; however, without limiting the scope of my instrument, system and method as expressed by these claims, in general terms, some, but not necessarily all, of their features are:

One, a light source emitting light at a frequency corresponding to an absorption line of water at a wavelength of 1871 nanometers plus or minus 2 nanometers is used in my instrument. The light source is positioned to emit light through a gas sample, and a detector is positioned and configured to detect the intensity of light passing through the gas sample.

Two, a cell member through which the gas sample passes is in communication with a laser diode as the light source. The laser diode has a temperature controller that maintains the laser diode at a predetermined set-point temperature.

Three, a mirror system within the cell member is configured to reflect the light internally so the light makes multiple passes prior to exiting the cell member. A photo-detector positioned nearby the cell member detects the intensity of light passing through the gas and exiting the cell member.

Four, an electronic circuit is coupled to the detector for determining the level of water vapor in the gas sample based on the detected intensity of light exiting the cell member. The control circuit is coupled to the photo-detector and this circuit includes a microprocessor and a display device. The microprocessor sets the parameters of the laser diode and the operation thereof so the laser diode emits light at a wavelength of 1871 nanometers plus or minus 2 nanometers. The display device shows the amount of water vapor detected in the gas sample.

My gas sampling and analyzing system comprises a first housing containing my analyzer instrument disclosed herein and a second separate housing containing the gas sampling device disclosed in U.S. Utility patent application Ser. No. 15/782,697, a copy attached hereto as Appendices A1 an A2. There is a fiber optical connection between the laser light source of my analyzer instrument and the gas sampling device, which is configured to avoid collecting sample gas therein that may be a source of ignition. In other words, the gas sampling device is intrinsically safe; and it comprises a compact block member, a manually operable metering valve system, a light transmission pathway, and a light collection system.

The compact block member includes a sealed gas passageway through the block member that provides a flow path for sampled gas. The passageway is configured to eliminate dead space along said flow path. The manually operable metering valve system is in communication with the flow path and this valve system regulates the flow of gas along the flow path. The light transmission pathway is along the gas passageway over which multiple passes of light propagate, and the light collection system includes a light detector positioned to collect light after making multiple passes. The flow path has a length that is less than 36 inches, and the gas sampling device has a length less than 16 inches, a depth less than 16 inches, and a height less than 16 inches.

The laser light source may be a laser diode having a temperature controller that maintains the laser diode at a predetermined set-point temperature. The light collection system may include a mirror system having a plurality of spaced apart mirrors configured to reflect the light internally over the light transmission pathway. An electronic control circuit regulates the operation of the laser diode, and this circuit includes a microprocessor that sets the parameters of the laser diode and the operation thereof so the laser diode emits light at a frequency corresponding to an absorption line of water at a wavelength of 1871 nanometers plus or minus 2 nanometers. The circuit may also include a display device for showing the amount of water vapor in the sampled gas.

My method of detecting trace amounts of water vapor in a gas comprises analyzing the gas using tunable diode laser absorption spectroscopy at a wavelength of 1871 nm plus or minus 0.5 nm.

DESCRIPTION OF THE DRAWING

Some embodiments of my instrument and method are discussed in detail in connection with the accompanying drawing, which is for illustrative purposes only. This drawing includes the following figures (Figs.), with like numerals and letters indicating like parts:

FIG. 4 is a front view of a system employing my analyzer instrument contained in one housing and in a separate housing a gas sampling device.

FIG. 5 is a side view of the system shown in FIG. 4 taken along line 5-5 of FIG. 4.

GENERAL

Natural Gas:

Main line natural gas consists primarily of methane ($CH_4$, 85-98%), with typically 0-4% carbon dioxide ($CO_2$), 0-6% ethane ($C_2H_6$), and smaller amounts of higher hydrocarbons such as propane, butane, etc. In terms of spectral interference when using second harmonic (2f) detection, the most troublesome compounds are the lower molecular weight molecules because these gases have sharper absorption features that are more separated in wavelength than the heavier gases (higher molecular weight) the more densely packed the absorption lines are, and at typical measurement pressures near 1-2 bar the absorption spectrum consists of broad "humps" rather than sharp and narrow absorption features for which 2f detection is optimized. So for butane ($C_4$), pentane ($C_5$) and higher hydrocarbons spectral interference issues are usually not a problem as long as the wavelength chosen for measurement of $H_2O$ is well away from a strong band of these gasses. CO2 has no absorption bands near 1871 nm so there is zero spectral interference under any circumstances. The 1871 nm band is located within a gap in the spectrum where only a very weak band is present.

Figure 1:
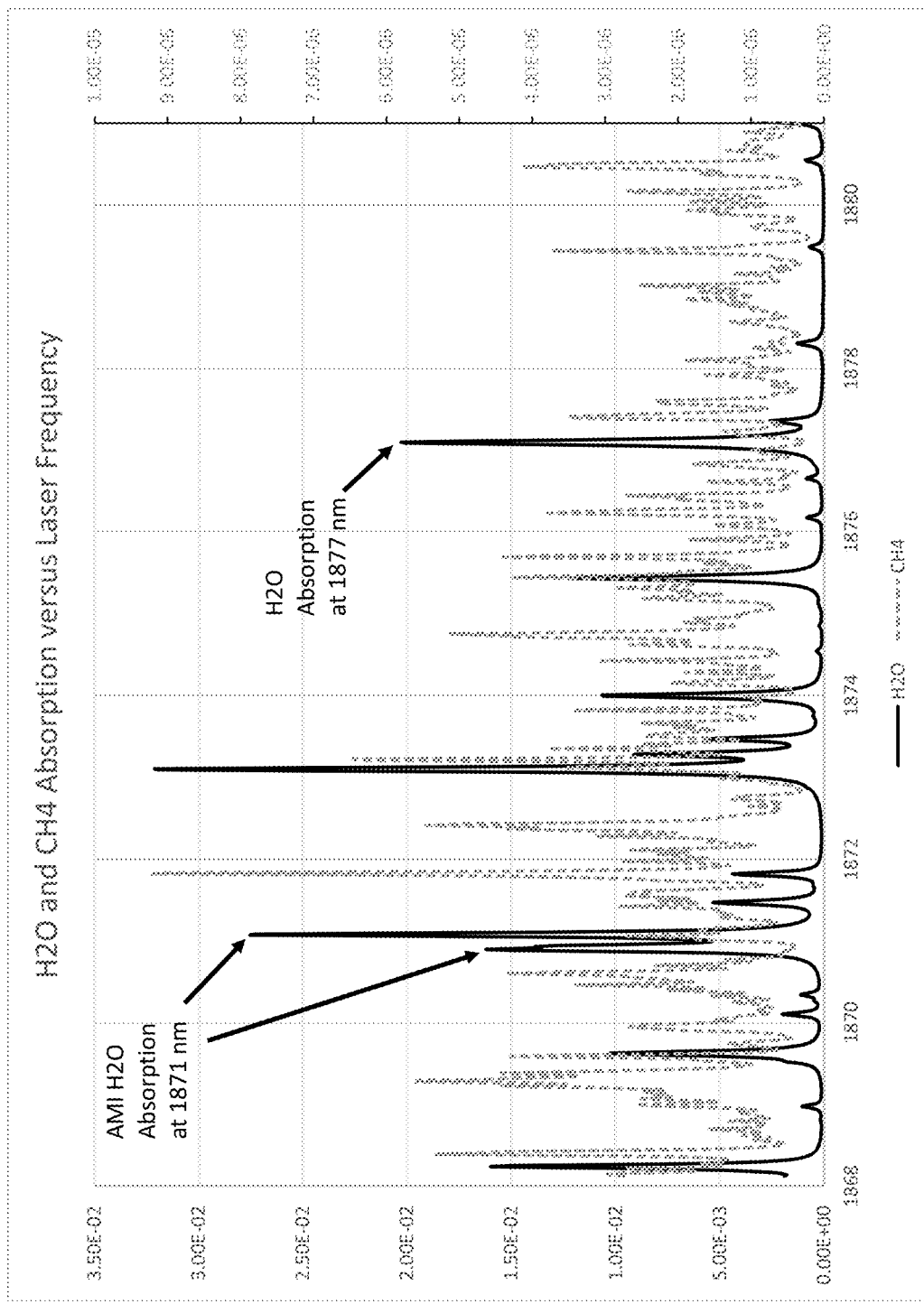
FIG. 1 is a gas (methane and higher molecular weight hydrocarbons and water) enlarged absorption spectra in the 1870-1880 micron region with methane absorption lines shown in dotted lines and water vapor absorption lines shown in solid lines, contrasting the wavelengths of 1871 microns verses 1877 microns.

Wavelength Considerations:

FIG. 1 shows examples of Fourier transform absorption spectra for $CH_4$ and $H_2O$ in the region most suitable for measuring $H_2O$ in natural gas. Interference by $CH_4$ is a major problem throughout the infrared and near infrared wavelength region, and it is the key consideration when choosing an $H_2O$ feature to measure. The region short of 1830 nm is not suitable for measuring $H_2O$ because the $CH_4$ absorption is so strong that nearly 100% of the light is absorbed for even modest absorption path lengths. Beyond about 1940 nm the $H_2O$ band starts to tail off and the absorption lines get very weak. The "sweet spot" for $H_2O$ measurement is therefore between about 1830-1940 nm.

FIG. 1 is a blowup of the 1850-1900 nm region with several target $H_2O$ lines indicated and the companies using them based on published information. The results of my improved instrument (AMI Model 4010BR FIGS. 4 and 5) are designated as AMI. None of these target $H_2O$ lines are completely clear of $CH_4$, and in principle any of them could be used to measure $H_2O$ (there is no interfering CO2 absorption in this region to worry about). No matter which $H_2O$ line is used, the spectrum processing algorithms have to manage the interfering absorption by $CH_4$, and this can be done in similar ways for any of these target $H_2O$ lines. Ametek has chosen 1854 nm (presumably) because it is the strongest $H_2O$ line in the region, but it is also the most interfered with by $CH_4$. SpectraSensors is using 1877 nm, which is a slightly weaker line but less interfered with by $CH_4$. The 1871 nm line is of similar strength to 1877 nm. Moreover, the 1871 nm line consists of two adjacent $H_2O$ lines that overlap. This is an advantage for "area under the curve" processing and produces a greater net signal to work with than simply using the amplitudes of the signals. Nevertheless, using the amplitudes of the signals is also a viable approach (and both can be done in software simultaneously).

2f Spectroscopy:

A common technique used for laser-based gas sensing is called second harmonic detection, or "2f" detection. This technique provides increased detection sensitivity at the expense of a more complicated control electronics subsystem, and a somewhat more difficult spectrum analysis process. It has been widely used since the 1970's with tunable diode lasers, and is the approach taken here.

Figure 2:
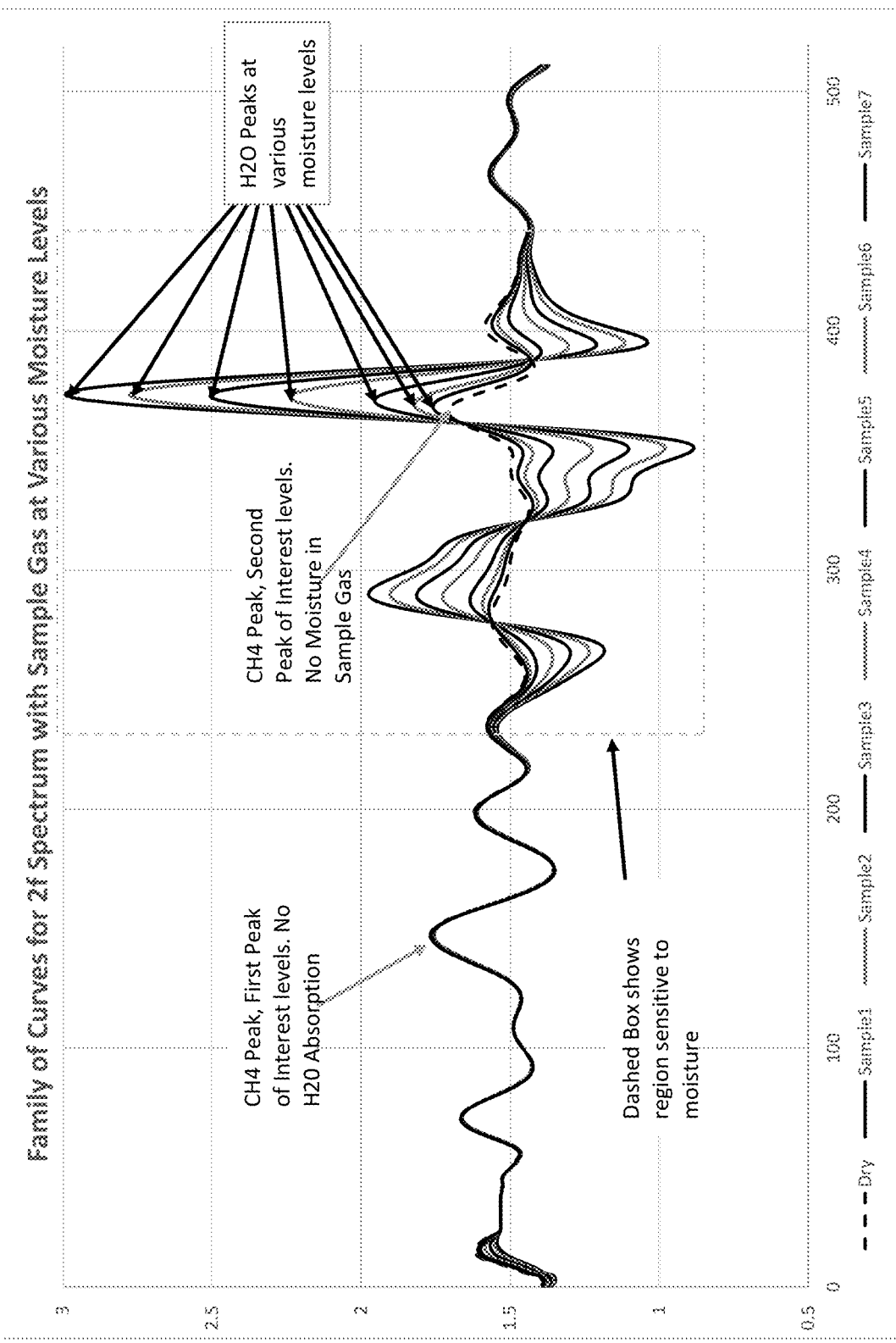
FIG. 2 is the 2f spectrum at the 1871 nm region used in my instrument and method for different concentrations of mixtures of methane and water vapor.

FIG. 2 shows examples of 2f spectra at the 1871 nm region in a small multi-pass absorption cell built for AMI. The horizontal axis is proportional to wavelength, which changes smoothly as the laser current is swept. The vertical axis is the 2f signal amplitude, and this spectrum contains absorption lines of both $H_2O$ and $CH_4$. This is the raw data that is processed for the $H_2O$ concentration. On the left shows a region where there is no $H_2O$ absorption. This region can be used to determine the $CH_4$ concentration, as well as to provide a reference signal to compare against the region to the right that contains the target $H_2O$ lines (as well as underlying $CH_4$ lines). The different shades of gray depict different levels of $H_2O$, and it is the difference in the amplitudes and/or areas of these features that are used to quantify the amount of $H_2O$ in the gas sample.

Signal processing of these types of 2f spectra can proceed via two basic methods. One is to use the difference in amplitudes of the various "bumps" across the spectrum and to relate those to the $H_2O$ concentration. The lower detection limit is determined by the smallest signal differences that can be reliably measured. The second is to integrate the separate oval regions shown in FIG. 1 to get the "area under the curve" of each section, then to ratio these to derive the $H_2O$ concentration. Since both of these signal or spectrum processing methods are implemented purely in the software program 12a (FIG. 3), both can be utilized and compared to determine which is most appropriate for my instrument. Both pressure (in particular) and temperature (to a lesser extent) impact the exact "shape" of the 2f spectral features. Since neither of these parameters pressure (P) and temperature (T) are held constant in the AMI instrument, it is necessary to build into the software program 12a calibration polynomials that quantify the changes in the 2f spectrum with pressure and temperature so that the correct $H_2O$ value can be extracted.

From measurements to date, the lower detection limit for $H_2O$ is in the range 0.25 pounds of $H_2O$ per million standard cubic feet of $CH_4$ (lb./mmscf). This standard unit used in the natural gas industry equals 20.5 parts per million by volume (ppmv). This is without any active control of the pressure (P) and temperature (T). The spectrum signal-to-noise ratio (SNR) produces a lower detection limit of approximately 0.25 lb. at a fixed P and T. Measurements still need to be made over ranges in P and T before this can be confirmed over the full expected operational range, but if the base spectrum SNR is sufficient for a lower detection limit of 0.25 lb. or better, then it should be possible via appropriate lab calibrations to easily maintain this level in the field. The typical specification for a base instrument such as this is a 0-20 lb. range with a lower detection limit of 0.5 lb. My analyzer instrument cuts the minimum detection limit in half Methane Measurement:

As shown in FIG. 1, there is a peak at the left side of the 2f spectrum that is caused by the absorption of laser light from methane ($CH_4$) gas in the sample cell. Because this isolated $CH_4$ peak is within the same laser scan as the desired water absorption peak at 1871 nm it is possible to accurately measure the $CH_4$ concentration in addition to the water concentration.

Figure 3:
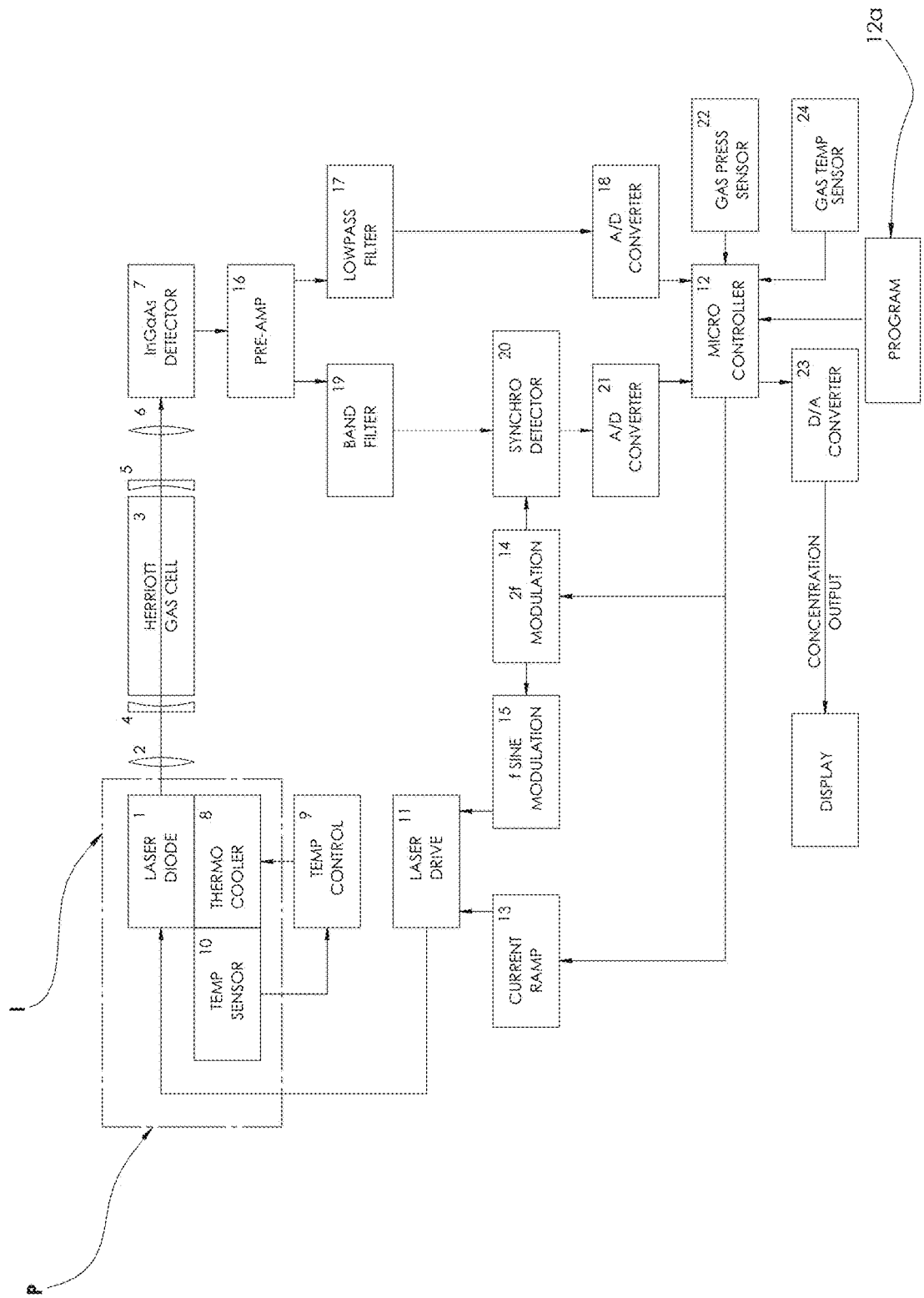
FIG. 3 is a schematic diagram of one embodiment of my analyzer instrument.

Peak Subtraction:

As FIG. 1 depicts, as the water concentration is increased the $H_2O$ peak height increases. The $H_2O$ peak height is directly proportional to the water concentration. Note, however, that even with dry $CH_4$ there is still some absorption at the location of the $H_2O$ peak due to the underlying $CH_4$ absorption. Typically, a constant value is subtracted from the $H_2O$ peak height to account for the underlying $CH_4$. However, if the amount of $CH_4$ changes that constant peak height is no longer the correct value to subtract. Variation in the underlying $CH_4$ peak height adds an uncertainty to the calculation of the water concentration and reduces the accuracy of current instruments. Since it is desirable to have the highest possible accuracy, the uncertainty in the underlying $CH_4$ peak height should be reduced. The spectrum includes a peak at the left side that does not change with water concentration. The height of this peak as well as the height of the water peak is measured by a microcontroller or microprocessor 12 that has the program 12a that processes a signal from light detector 7 as shown in FIG. 3. It is known that the various $CH_4$ peak heights are always in a constant ratio to each other. Therefore, by measuring the left hand $CH_4$ peak one can calculate the exact height of the $CH_4$ peak that lies at the water peak location. Subtracting out this exact peak height instead of a constant value reduces uncertainty to the calculation of the water concentration, and therefore, the desired increase in accuracy. This calculation is automatically conducted by the microprocessor 12 according to its program 12a.

Integrated Laser Package:

Typical TDLAS analyzers use a laser that is packaged alone in a TO type can or package P (FIG. 3). The temperature of the laser is controlled by controlling the temperature of a heat sink to which the laser package is attached. In practice, there is always some temperature between the heat sink and the actual laser chip. Since the laser wavelength is strongly dependent on the laser chip temperature there will be some variation in the temperature control of the laser chip. The instrument I has a laser chip that is mounted directly on top of a thermoelectric cooler 8 inside of the laser package. This tight coupling between the thermoelectric cooler 8 and the laser chip provides a more stable laser temperature (and therefore instrument stability) over a wide range of ambient operating temperatures.

DETAILED DESCRIPTION OF SOME ILLUSTRATIVE EMBODIMENTS

FIG. 3

As depicted in FIG. 3, one embodiment of my instrument is designated by the letter I. In my instrument I, near-infrared light from a laser diode 1 is collimated by an aspheric lens 2 and passes through a Herriott cell 3. The light makes multiple passes through the Herriott cell 3 because of reflections between concave mirrors 4 and 5. The light exiting the Herriott cell 3 is focused by another aspheric lens 6 onto an extended InGaAs photo-detector 7. When the wavelength of light from the laser corresponds to an absorption line of the gas in the Herriott cell 3, the intensity of light reaching the InGaAs detector 7 will be reduced.

The wavelength of the laser is determined by its temperature and drive current. The temperature of the laser is determined by a thermoelectric cooler 8 that is in contact with the laser substrate and mounted internally to a laser package P. The thermoelectric cooler 8 is controlled by the output of the PID temperature controller circuit 9. Feedback from the thermistor temperature sensor 10, also in thermal contact with the laser's substrate, maintains the laser diode 1 to better than 0.1° C. of the set-point temperature. The thermoelectric cooler 8 will also heat when the controller circuit's 9 output voltage is reversed. By using an H-bridge circuit for the output of the temperature controller 9 the laser diode 1 can be maintained at a precise temperature, ideally around 30° C., in ambient temperatures between −10° C. and 50° C. The exact temperature to be maintained depends on the specific laser characteristics.

The laser current is provided by an emitter follower output of the laser drive circuit 11. This current is the sum of a current ramp 13 that scans the laser output wavelength over a narrow range, typically less than 1 nm, in a few tenths of a second and a small sine-wave modulation at a high frequency on the order of 10 KHz. The sine wave modulation is produced by dividing down a square-wave signal at twice the frequency. All of the laser current parameters are set by the microprocessor controller 12. Those parameters include the starting and ending currents of the current ramp, the speed of the current ramp, and the amplitude and frequency of the square-wave. Since the sine-wave is derived from the square-wave that too is controlled by the microprocessor controller 12.

When the laser temperature and modulated current ramp are properly adjusted, the laser output wavelength will periodically sweep across the desired absorption line of the gas in the Herriott cell 3. The resulting signal from the detector is amplified by a trans-conductance pre-amplifier 16. The signal from the pre-amplifier 16 looks similar to the laser current drive signal, except that it is reduced in strength when the laser wavelength equals the absorption line wavelength. Because the modulation frequency is much higher than the ramp rate the two signal components can be separated. This is done by putting the pre-amp output to a low pass filter 17 and a band pass filter 19. The output of the band pass filter is digitized by the A/D converter 18, usually at 256, 512, or 1024 points across the scan. The signal from the low pass filter 17, usually called the DC signal, looks like a ramp with a dip in the middle where the absorption from the gas in the Herriott cell 3 is greatest. The area between the dip and straight line along the top of the ramp is proportional to the natural log of the density of the absorbing gas. Although this signal can be used to calculate the density of the absorbing gas it is noisy and has a high lower limit of detection.

The band pass filter 19 is tuned to two times the modulation frequency. The amplitude modulation of this second harmonic signal is proportional to the second derivative of the absorption strength. Further noise reduction is accomplished by using a synchronous detector 20 to filter out any components of the second harmonic signal that are within the pass band but not in phase with the laser modulation. This signal is usually called the 2f signal. A second A/D converter 21 converts the signal into data points that can be analyzed by the microprocessor controller 12. Instead of a Lorentzian shape like the DC signal has, the second derivative is a peak with a dip on each side of it. Because the dips are usually asymmetric the average of the two dips is subtracted from the peak. The density of the absorbing gas in the Herriott cell 3 is proportional to the dip-to-peak height of the signal. The dip-to-peak value is normalized by the value of the DC signal to account for gain factors in the band pass filter and the synchronous detector.

Since the density of the absorbing gas in the cell 3 is only the partial pressure in the cell, it is necessary to divide the partial pressure by the total pressure measured by a pressure sensor 22 to get the concentration of the absorbing gas. The pressure sensor 22 needs to measure the absolute pressure in the Herriott cell 3. The final concentration value can be calculated by the microprocessor controller 12, converted to an analog output signal by a D/A converter 23, and shown as a percentage reading on a liquid crystal display device LCD.

Details of the spectrum analysis performed by the microprocessor controller 12, include, for example, the pressure in the cell 3 causes collisions between the absorbing gas molecules. The collisional energy can add or subtract to the absorption energy and cause the absorption peak to broaden and shorten. The area under the DC peak stays constant, but the 2f signal is reduced by the broadening. The 2f peak height is also affected by the gas temperature in the cell 3. The measured dip-to-peak height needs to be adjusted for cell pressure and cell temperature measured by a gas temperature sensor 24. The pressure broadening is dependent on the relative sine-wave modulation amplitude and is calibrated along with temperature dependence for every analyzer during final test. At high concentrations there can be non-linearity in the response that must also be corrected for at final test with another second or third order polynomial function.

FIGS. 4 Through 7

Figure 7:
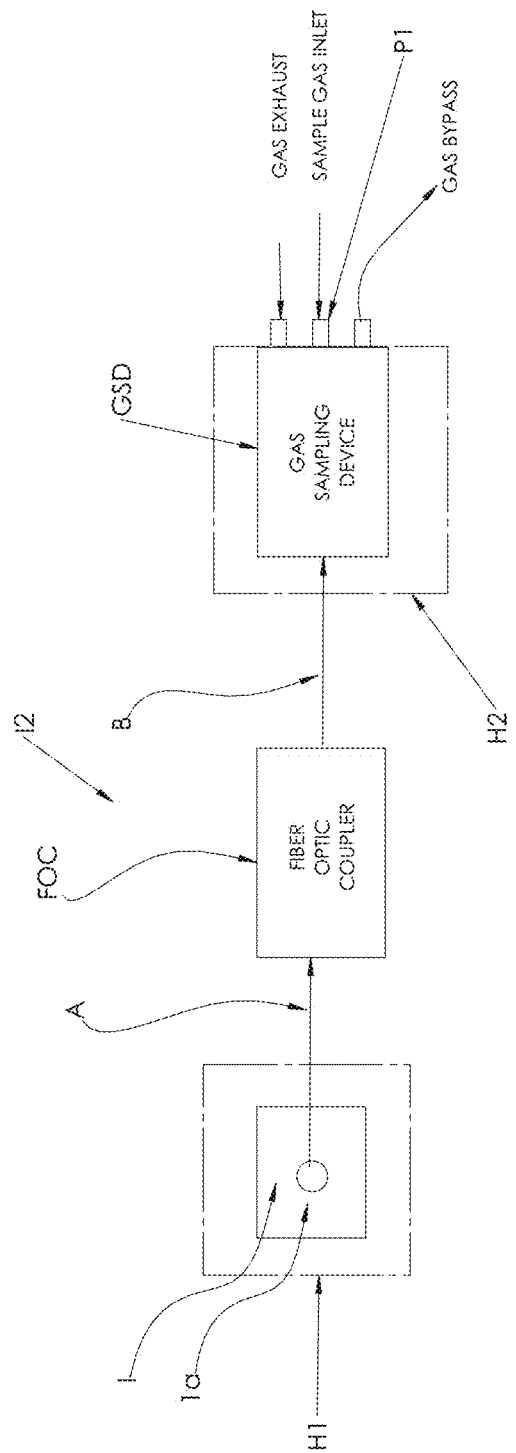
FIG. 7 is a schematic diagram of the fiber optical connection between a laser within a laser housing and the explosion resistant gas-sampling device in the other housing.

As illustrated in FIG. 7, a commercial embodiment of my gas sampling and analyzing system is designated by the alphanumerical symbol 12. In my system 12, two separate housings are employed: housing H1 for the laser package P and housing H2 for a gas sampling device GSD. The gas-sampling device GSD is the subject of my Utility Patent application Ser. No. 15/782,697, entitled Gas Sampling Device and Method, filed Oct. 12, 2017, copy attached in Appendices A1 and A2. Because of the voltage connections to the electrical components of the laser package P, there is a risk of sparking that could ignite any natural gas being sampled and tested. By using a separate a gas sampling device GSD that does not employ any electrical components, the likelihood of the natural gas flowing into the gas sampling device GSD is essentially eliminated.

Figure 6:
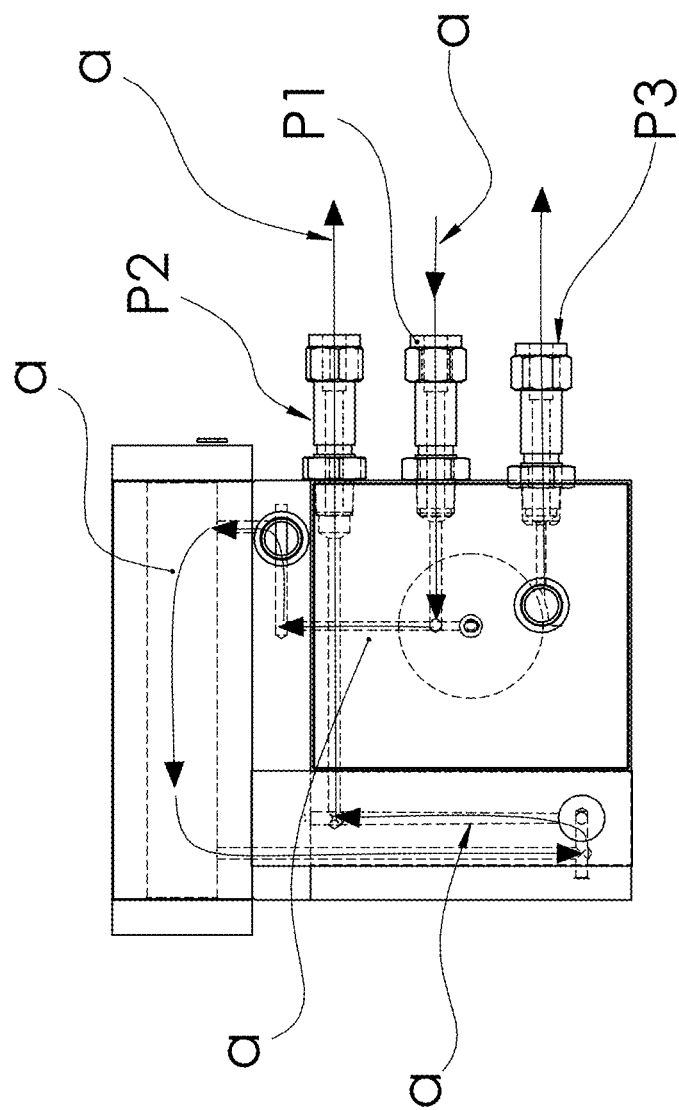
FIG. 6 is a side view of the gas-sampling device used with my system shown in FIGS. 4 and 5.

As depicted in FIG. 7, the laser light from an output 1a of the laser diode 1 is directed to the Herriott gas cell 3 by means of a fiber optic coupler or cable FOC. The fiber optic cable FOC has a first segment A feeding light from the output 1a to an explosion proof fiber optic cable FOC. The second segment B of the fiber optic cable FOC feeds the laser light into a lens L, which is mounted in the gas sampling device GSD. As depicted in FIG. 6 sample gas enters the gas sampling device GSD through a port P1, flows along a flow path FP provided by an internal passageway shown by arrows a, and exits an exhaust port P2. A bypass port P3 may also be employed. The body of the gas sampling device GSD may be formed by a plurality of metal blocks fastened together with conventional fasteners.

Figure 3A:
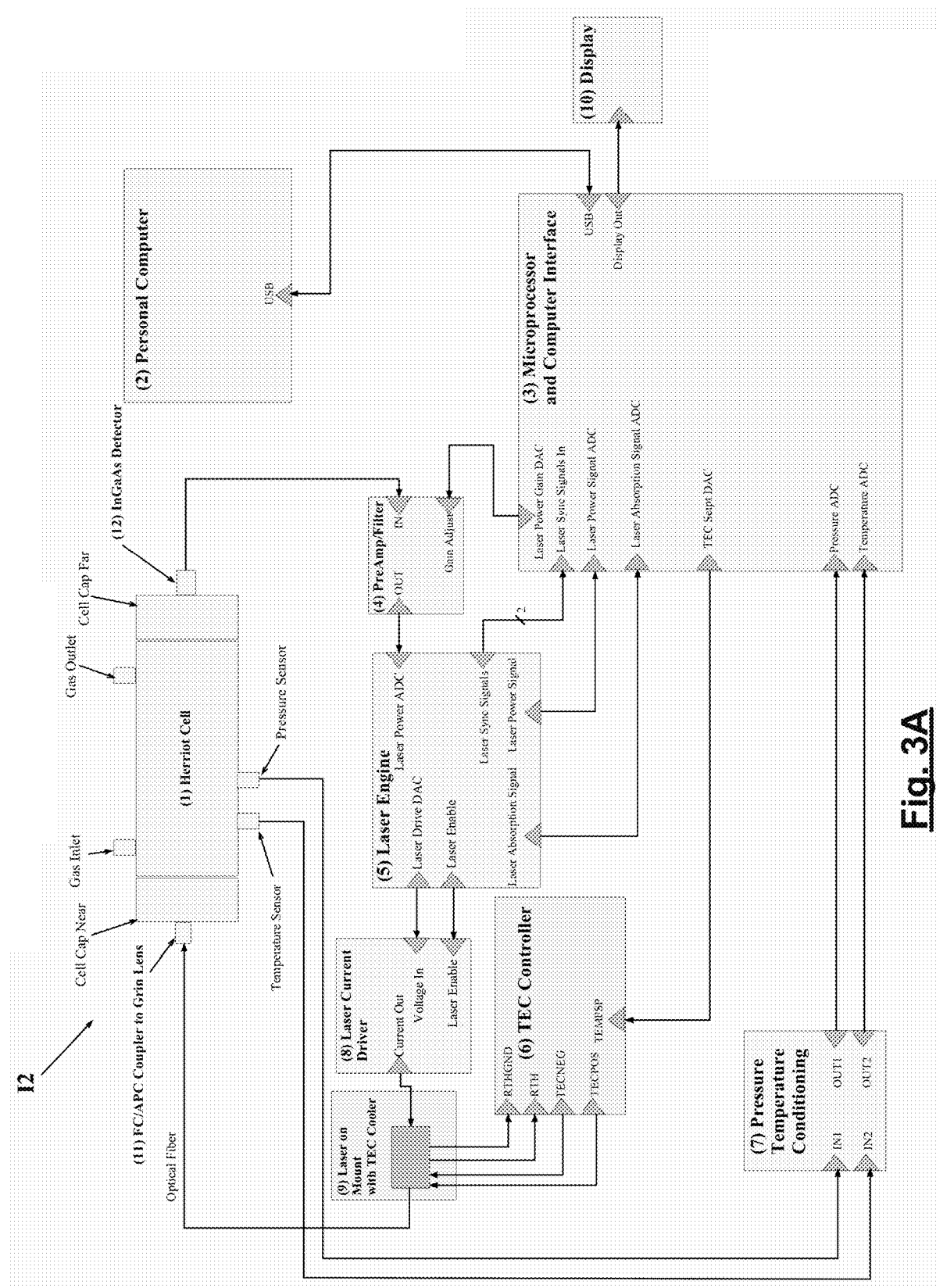
FIG. 3A is a schematic diagram of an alternate embodiment of my analyzer instrument.

FIG. 3A-Alternate Embodiment

In an alternate embodiment of my analyzer illustrated in FIG. 3A, only one lens, a gradient index (GRIN) lens, may be used. In this embodiment, the lens 2 is replaced by the GRIN lens (11) and the lens 4 is eliminated.

As depicted in FIG. 3A an alternate embodiment of my instrument is designated by the letter 12. In my instrument 12, near-infrared light from a laser diode in the Laser Mount with TEC cooler (9) is collimated by a Grins Lens (11) and passes through a Herriott cell (1). The light makes multiple passes through the Herriott cell (1) because of reflections between concave mirrors in the Cell Cap Near and Far Included with the Herriot Cell (1). The light is then detected by an extended InGaAs photo-detector (12). When the wavelength of light from the laser corresponds to an absorption line of the gas in the Herriott cell (1), the intensity of light reaching the InGaAs detector (12) will be reduced.

The wavelength of the laser is determined by its temperature and drive current. The temperature of the laser is determined by a thermoelectric cooler that is in contact with the laser substrate and mounted internally to a laser package (9). The laser package contains both the laser and the thermoelectric cooler. The thermoelectric cooler is controlled by the output of the PID temperature controller circuit (6). Feedback from the thermistor temperature sensor in the laser package (9) that is in thermal contact with the laser's substrate, maintains the laser diode in the Laser Package (9) to better than 0.1° C. of the set-point temperature. The thermoelectric cooler in the laser package (9) will also heat when the controller circuit's (6) output voltage is reversed. By using an H-bridge circuit for the output of the temperature controller 6 the laser diode in the laser package (9) can be maintained at a precise temperature, ideally around 30° C., in ambient temperatures between −10° C. and 50° C. The exact temperature to be maintained depends on the specific laser characteristics.

The laser current is provided by an emitter follower output of the laser drive circuit (8). This current is the sum of a current ramp created by the laser engine (5) that scans the laser output wavelength over a narrow range, typically less than 1 nm, in a few tenths of a second and a small sine-wave modulation at a high frequency on the order of 10 KHz. The sine wave modulation is produced by dividing down a square-wave signal at twice the frequency. All of the laser current parameters are set by the microprocessor controller (3). Those parameters include the starting and ending currents of the current ramp, the speed of the current ramp, and the amplitude and frequency of the square-wave. Since the sine-wave is derived from the square-wave that too is controlled by the microprocessor controller (3).

When the laser temperature and modulated current ramp are properly adjusted, the laser output wavelength will periodically sweep across the desired absorption line of the gas in the Herriott cell (1). The resulting signal from the detector is amplified by a trans-conductance pre-amplifier (4). The signal from the pre-amplifier (4) looks similar to the laser current drive signal, except that it is reduced in strength when the laser wavelength equals the absorption line wavelength. Because the modulation frequency is much higher than the ramp rate the two signal components can be separated. This is done by putting the pre-amp output to a low pass filter (17) and a band pass filter in the laser engine (5). The output of the band pass filter is digitized by the A/D converter in the microprocessor system (3), usually at 256, 512, 1024, 2048, or 5000 points across the scan. The signal from the low pass filter from laser engine (5), usually called the DC signal, looks like a ramp with a dip in the middle where the absorption from the gas in the Herriott cell (1) is greatest. The area between the dip and straight line along the top of the ramp is proportional to the natural log of the density of the absorbing gas. Although this signal can be used to calculate the density of the absorbing gas it is noisy and has a high lower limit of detection.

The band pass filter in the Laser Engine is tuned to two times the modulation frequency. The amplitude modulation of this second harmonic signal is proportional to the second derivative of the absorption strength. Further noise reduction is accomplished by using a synchronous detector in the Laser Engine to filter out any components of the second harmonic signal that are within the pass band but not in phase with the laser modulation. This signal is usually called the 2f signal. A second A/D converter in the microprocessor controller (3) converts the signal into data points that can be analyzed by the microprocessor controller (3). Instead of a Lorentzian shape like the DC signal has, the second derivative is a peak with a dip on each side of it. Because the dips are usually asymmetric the average of the two dips is subtracted from the peak. The density of the absorbing gas in the Herriott cell (1) is proportional to the dip-to-peak height of the signal. The dip-to-peak value is normalized by the value of the DC signal to account for gain factors in the band pass filter and the synchronous detector.

Since the density of the absorbing gas in the Herriot cell (1) is only the partial pressure in the cell, it is necessary to divide the partial pressure by the total pressure measured by a pressure sensor in the Herriot Cell (1) to get the concentration of the absorbing gas. The pressure sensor in the Herriot Cell (1) needs to measure the absolute pressure in the Herriott cell (1). The final concentration value can be calculated by the microprocessor controller (3), converted to an analog output signal by a pressure temperature conditioning (7) and the microprocessor D/A converter (3), and shown as a percentage reading on a display device (10).

Details of the spectrum analysis performed by the microprocessor controller (3), include, for example, the pressure in the Herriot cell (1) causes collisions between the absorbing gas molecules. The collisional energy can add or subtract to the absorption energy and cause the absorption peak to broaden and shorten. The area under the DC peak stays constant, but the 2f signal is reduced by the broadening. The 2f peak height is also affected by the gas temperature in the Herriot cell (1). The measured dip-to-peak height needs to be adjusted for cell pressure and cell temperature measured by a gas temperature sensor in the Herriot Cell (1). The pressure broadening is dependent on the relative sine-wave modulation amplitude and is calibrated along with temperature dependence for every analyzer during final test. At high concentrations there can be non-linearity in the response that must also be corrected for at final test with another second or third order polynomial function.

The personal computer (2) communicates with the microprocessor controller (3) to verify correct operation of the system, download information for analysis, upload firmware to the Microprocessor Controller, and change internal variables in the microprocessor controller (3) that relate to the operation of the system.

SCOPE OF THE INVENTION

The above presents a description of the best mode I contemplate of carrying out my instrument, system, and method for detecting water vapor in gas, and of the manner and process of making and using them, in such full, clear, concise, and exact terms as to enable a person skilled in the art to make and use. My instrument, system, and method are, however, susceptible to modifications and alternate constructions from the illustrative embodiments discussed above which are fully equivalent. Consequently, it is not the intention to limit my instrument, system, and method to the particular embodiments disclosed. On the contrary, my intention is to cover all modifications and alternate constructions coming within the spirit and scope of my instrument, system, and method as generally expressed by the following claims, which particularly point out and distinctly claim the subject matter of my invention:

The invention claimed is:

1. An analyzer instrument for detecting water vapor within a natural gas and/or methane gas stream comprising:
   a light source positioned to emit light and pass said light through the gas stream, and
   a detector is positioned to detect the intensity of light passing through the gas stream,
   said light source configured to emit light consisting of a frequency corresponding to an absorption line of water at a wavelength of 1871 nanometers plus or minus 2 nanometers, and
   an electronic circuit coupled to said detector for determining the level of water vapor in the gas based on the detected intensity.

2. An analyzer instrument for detecting water vapor within a natural gas and/or methane gas stream comprising:
   a cell member having a laser diode for holding the gas stream,
   said laser diode having a temperature controller that maintains the laser diode at a predetermined set-point temperature,
   a mirror system configured to reflect the light internally within the cell member so the light makes multiple passes prior to exiting the cell member,
   a photo-detector positioned at an end of the cell member to detect the intensity of light passing through the gas stream and exiting the cell member, and
   a control circuit coupled to said detector for determining the level of water vapor in the gas stream based on the detected intensity including
      a microprocessor configured to set the parameters of the laser diode and the operation thereof so the laser diode emits light consisting of a wavelength of 1871 nanometers plus or minus 2 nanometers, and
      a display device for showing the amount of water vapor detected in the gas.

3. In an absorption spectroscopy method for detecting water vapor within a natural gas and/or methane gas stream comprising:
   passing through the gas stream light consisting of a frequency corresponding to an absorption line of water at a wavelength of 1871 nanometers plus or minus 2 nanometers, and
   detecting the intensity of light passing through the gas sample and determining the level of water vapor in the gas stream based on the detected intensity.

* * * * *